US009259486B2

(12) United States Patent
Koenig

(10) Patent No.: US 9,259,486 B2
(45) Date of Patent: Feb. 16, 2016

(54) METHOD AND SYSTEM FOR CALCULATING A QUANTIFICATION INDICATOR FOR QUANTIFYING A DERMAL REACTION ON THE SKIN OF A LIVING BEING

(71) Applicant: Commissariat a l'energie atomique et aux energies alternatives, Paris (FR)

(72) Inventor: Anne Koenig, Saint Martin D'Uriage (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 73 days.

(21) Appl. No.: 14/169,572

(22) Filed: Jan. 31, 2014

(65) Prior Publication Data
US 2014/0241994 A1 Aug. 28, 2014

(30) Foreign Application Priority Data
Feb. 1, 2013 (FR) ...................................... 13 50905

(51) Int. Cl.
| A61K 49/00 | (2006.01) |
| A61B 5/00 | (2006.01) |
| G01N 21/47 | (2006.01) |
| G06F 19/00 | (2011.01) |

(52) U.S. Cl.
CPC ........... *A61K 49/0006* (2013.01); *A61B 5/0075* (2013.01); *A61B 5/411* (2013.01); *A61B 5/445* (2013.01); *G01N 21/47* (2013.01); *G06F 19/70* (2013.01)

(58) Field of Classification Search
CPC .. A61K 49/0006; A61B 5/0075; A61B 5/411; A61B 5/445; G01N 21/47; G06F 19/70
See application file for complete search history.

(56) References Cited

U.S. PATENT DOCUMENTS

| 2010/0160754 A1* | 6/2010 | Durkin et al. ................. 600/342 |
| 2011/0124987 A1 | 5/2011 | Papazoglou et al. |
| 2012/0130257 A1 | 5/2012 | Heanue et al. |

OTHER PUBLICATIONS

Narasimhan Rajaram, Tri H. Nguyen, and James W. Tunnell, "Lookup table-based inverse model for determining optical properties of turbid media" Journal of biomedical Optics, 13(5), 2008.*

(Continued)

*Primary Examiner* — Tse Chen
*Assistant Examiner* — Joanne Hoffman
(74) *Attorney, Agent, or Firm* — Troutman Sanders LLP

(57) ABSTRACT

This method is designed for calculating a quantification indicator for quantifying a dermal reaction on a skin having several chromophores. The method includes illumination of a zone to be characterized on the skin, the skin reaction being included in the zone to be characterized; and measurement of the spectrum of a back scattered radiation coming from the skin after illumination of said zone to be characterized. The method also includes determination, according to the measured spectrum, of an absorption coefficient value for the zone to be characterized, and calculation, according to the absorption coefficient value, of each chromophore concentration. The method includes calculation of the quantification indicator according to each calculated chromophore concentration. The method includes determination, according to the measured spectrum, of a diffusion coefficient value of the zone to be characterized, and the quantification indicator is further calculated according to the diffusion coefficient value.

23 Claims, 6 Drawing Sheets

(56) References Cited

OTHER PUBLICATIONS

G.N. Stamatas, B.Z. Zmudzka, N. Kollias, and J.Z. Beer, "In vivo measurement of skin erythema and pigmentation: new means of implementation of diffuse reflectance spectroscopy with a commercial instrument", British Journal of Dermatology, 159:683-690, 2008.*

Sheng-Hao Tseng, Alexander Grant, and ANthony J. Durkin, "In vivo determination of skin near-infrared optical properties using diffuse optical spectroscopy", J Biomed Opt., 13(1), 2008.*

Mitsuharu Miwa, Yukio Ueda, and Britton CHance, "Development of Time Resolved Spectroscopy System for Quantitative Non-invasive Tissue Measurement", SPI vol. 2389.*

Philippe THueler, Igor Charvet, Frederic Bevilacqua, M. St. Ghislain, G. Ory, Pierre Marquet, Paolo Meda, Ben Vermeulen, Christian Depeursinge, "In vivo endoscopic tissue diagnostics based on spectroscopic absorption, scattering, and phase funtion properties", Jounal of Biomedical Optics 8(3): 495-503, 2003.*

Kollias N, et al, "Interpreting diffuse reflectance for in vivo skin reactions in terms of chromophores", Journal of Biophotonics, vol. 3, No. 1-2, 2010, pp. 15-24.

Koenig A, et al, "Diffuse reflectance spectroscopy: a clinical study of tuberculin skin tests reading", Proceedings of SPIE, vol. 8592, 2013, pp. 85920S-85920S-8.

International Search Report and Written Opinion, dated Dec. 5, 2013, which issued during the prosecution of French Patent Application No. 1350905, which corresponds to the present application.

* cited by examiner

METHOD AND SYSTEM FOR CALCULATING A QUANTIFICATION INDICATOR FOR QUANTIFYING A DERMAL REACTION ON THE SKIN OF A LIVING BEING

CROSS-REFERENCE TO RELATED APPLICATIONS

This application claims priority under 35 U.S.C. §119 to French Patent Application No. 1350905, filed Feb. 1, 2013, the disclosure of which is herein incorporated by reference in its entirety.

FIELD OF THE INVENTION

The present invention relates to a method for calculating a quantification indicator for quantifying a dermal reaction on the skin of a living being, such as a dermal reaction following the injection of an active ingredient. In the sections hereinafter, the dermal reaction on the skin is also referred to as skin reaction.

BACKGROUND

One method of calculating to find a dermal reaction, prior to the present invention, included the illumination of a zone to be characterized on the skin via an excitation light beam emitted by a source of light, the skin reaction being included in the zone to be characterized, the measurement, by means of a spectrometer, of the spectrum of a back scattered radiation coming from the skin as a result of the illumination of said zone to be characterized, the determination, on the basis of the measured spectrum and for at least one given value of the wave length of the light beam, of a value of the absorption coefficient for the zone to be characterized, the calculation, on the basis of the or each determined value of the absorption coefficient, of the concentration of at least one chromophore in the skin, and the calculation, of the quantification indicator for quantifying the dermal reaction on the basis of the previously calculated concentration of the or each chromophore.

The present invention also relates to a system for calculating such a quantification indicator.

The invention is applicable in particular to the calculation of an indicator for the quantification of a patient's skin reaction following the intradermal injection of an active ingredient for the implementation of a test for the presence of antibodies in the organism, the test being for example the test for tuberculosis after an injection of tuberculin. The quantification indicator is thus a function of the immune response.

The invention is also applicable to the calculation of an indicator for the quantification of the skin reaction following the injection of an active ingredient capable of causing an allergic skin reaction.

The invention is more generally applicable to the calculation of an indicator for the quantification of any dermal reaction, such as an inflammation reaction, an induration reaction, or even a reaction involving alteration of the skin.

The article "*Interpreting diffuse reflectance for in vivo skin reactions in terms of chromophores*" by Kollias et al, published in the journal entitled Journal of Biophotonics, in 2010, describes a method and a system for calculation of the aforementioned type. This article is a quantitative interpretation of skin reactions based on the measurements of reflectance of the skin, in particular forming the assumption that the attenuation of the light during its propagation through the skin, obeys the Beer-Lambert law.

The method of operation is as follows. The skin is illuminated with a light beam emitted from a source of white light, the measurements of reflectance of a back scattered radiation due to the illumination of the skin are then performed with the aid of a spectrometer. The concentrations of chromophores in the skin, in particular the concentrations of melanin, oxyhaemoglobin and deoxyhaemoglobin, are calculated from the measured reflectance values.

The absorbance of the skin is considered to be dependent upon chromophore concentrations calculated on the basis of the values of reflectance measured. In the case of the formation of pigments induced by a simulated solar radiation, the only chromophore concentration taken into consideration for the quantification is the concentration of melanin. In the case of an inflammation induced by histamine, the chromophore concentrations taken into account are the concentrations of oxyhaemoglobin ($HbO2$) and water. The effect of the diffusion is approximated by taking into consideration an additional chromophore. Thus, diffusion is considered comparable to absorption linked to the concentration of this new chromophore.

Finally, in this paper, the authors have established the evolution of these chromophores based on certain inflammations. However, they do not calculate an index to enable quantifying the reaction of the skin based on these concentrations. By the authors' own admission, the relationships between the concentrations of different chromophores have not been explored in an exhaustive manner and thus remain to be established.

For their part, the inventors have found that it was necessary to establish a multi parameter indicator, that is to say, one that takes into account the concentration of various chromophores thereby enabling the quantifying of the skin reaction following injection of the active ingredient. Moreover, they observed that such quantification carried out by using different concentrations of chromophores is not always very precise, and a certain number of results are incorrect, with the reaction for example being incorrectly indicated as positive (false positive), or on the contrary being indicated as negative whereas it is positive in actual fact (false negative).

SUMMARY

The object of the invention is therefore to provide a method and a system of calculation that makes it possible to improve the relevance of the calculated quantification indicator, while also allowing for the calculation of this indicator within the shortest possible time period after the original stimulation that causes the dermal reaction.

To this end, the object of the invention is to provide a method of calculation of the aforementioned type, wherein the method further includes—the determination, on the basis of the measured spectrum and for at least one given value of the wave length of the light beam, of a value for the diffusion coefficient of the zone to be characterized, and wherein the quantification indicator for quantifying the dermal reaction is also calculated on the basis of the or each determined value of the diffusion coefficient.

According to other advantageous aspects of the invention, the method of calculation includes one or more of the following characteristic features, taken individually or in accordance with all technically possible combinations during the step of calculation, the quantification indicator for quantifying the dermal reaction is calculated furthermore on the basis of the or each determined value of the absorption coefficient; the quantification indicator for quantifying the dermal reaction is calculated on the basis of an average value, such as the arithmetic average, of a plurality of values of the absorption coefficient, determined for a plurality of values of the wave length of the light beam comprised between 450 nm and 800 nm, preferably between 450 nm and 700 nm, and more preferably between 500 nm and 650 nm; the quantification indicator for quantifying the dermal reaction is calculated on the basis of an average value, such as the arithmetic average, of a plurality of values of the diffusion coefficient, determined for a plurality of values of the wave length of the light beam comprised between 450 nm and 800 nm, preferably between 650 nm and 800 nm, and more preferably between 740 nm and 760 nm; the quantification indicator for quantifying the dermal reaction satisfies the following equation:

$$IND = \alpha + \beta \times Ox + \gamma \times Deox + \delta \times Dif + \epsilon \times Abs$$

where IND represents the quantification indicator for quantifying the dermal reaction, $\alpha$, $\beta$, $\gamma$, $\delta$ and $\epsilon$ are predetermined coefficients for a given value of the time period between the moment of measurement of the spectrum of a back scattered radiation and the moment of injection of the active ingredient, with $\beta$, $\gamma$ and $\delta$ having non-null values, Ox and Deox represent the oxyhaemoglobin concentration and deoxyhaemoglobin concentration, respectively, for the zone to be characterized, Dif and Abs represent an average value, such as the arithmetic mean, respectively of the determined value or values of the diffusion coefficient of the zone to be characterized, and of the determined value or values of the absorption coefficient of the zone to be characterized. During the step of calculation of the concentration of the chromophore or chromophores, the concentration of the chromophore or chromophores is also calculated for a healthy zone of the skin on the basis of the value or values of the absorption coefficient for said healthy zone, and during the step of calculation, the quantification indicator for quantifying the dermal reaction is calculated on the basis of a difference between the concentrations of the or each chromophore of the healthy zone and of the zone to be characterized and on the basis of the difference or differences between the determined values of the diffusion coefficient of the healthy zone and the zone to be characterized; during the step of calculation, the quantification indicator for quantifying the dermal reaction is calculated additionally on the basis of the difference or differences between the determined values of the absorption coefficient of the healthy zone and the zone to be characterized; during the step of calculation of the concentration of the chromophore or chromophores, the concentration of the chromophore or chromophores is additionally also calculated for a healthy zone of the skin on the basis of the value or values of the absorption coefficient for said healthy zone, and the quantification indicator for quantifying the dermal reaction satisfies the following equation:

$$IND = \alpha' + \beta' \times \Delta Ox + \gamma' \times \Delta Deox + \delta' \times \Delta Dif + \epsilon' \times \Delta Abs$$

where IND represents the quantification indicator for quantifying the dermal reaction, $\alpha'$, $\beta'$, $\gamma'$, $\delta'$ and $\epsilon'$ are predetermined coefficients for a given value of the time period between the moment of measurement of the spectrum of a back scattered radiation and the moment of injection of the active ingredient, with $\beta'$, $\gamma'$ and $\delta'$ having non-null values, $\Delta Ox$ and $\Delta Deox$ represent respectively, a difference between the oxyhaemoglobin concentrations of the healthy zone and the zone to be characterized, and a difference between the deoxyhaemoglobin concentrations of the healthy zone and the zone to be characterized, $\Delta Dif$ and $\Delta Abs$ represent an average value, such as the arithmetic mean, respectively, of the difference or differences between the determined values of the diffusion coefficient of the healthy zone and the zone to be characterized, and of the difference or differences between the determined values of the absorption coefficient of the healthy zone and the zone to be characterized.

The zone of the skin is illuminated via an excitation optical fibre, and measurement of the spectrum is performed via a plurality of detection optical fibres connected to the spectrometer, the detection fibres being at different distances from the excitation fibre; and the determination, for at least one given value of the wave length of the light beam, of the value of the absorption coefficient, and the diffusion coefficient, respectively, is performed on the basis of the measured spectra for said different distances.

The method further includes the predetermination of a reference table including a plurality of values of the reflectance of the skin, each value of said table being predetermined for a respective pair of values of the absorption coefficient and the diffusion coefficient, at least one value of the reflectance of the zone to be characterized is measured with the use of the spectrometer during the step of measurement, and during the step of determination of the absorption coefficient and the diffusion coefficient, the pair of determined values of the absorption coefficient and the diffusion coefficient is that which minimises the error between the predetermined reflectance values of the reference table and the measured reflectance value or values, The zone of the skin is illuminated via an excitation optical fibre, and measurement of the spectrum is performed via a plurality of detection optical fibres connected to the spectrometer, the detection fibres being at different distances from the excitation fibre; and the predetermination of the reference table is carried out for said different distances, each value of said table being predetermined for a respective pair of values of the absorption coefficient and the diffusion coefficient and for said different distances, at least one value of the reflectance of the zone to be characterized being measured for each of said distances and with the use of the spectrometer during the measurement step. During the step of calculation of the concentration of the chromophore or chromophores, the concentration of the chromophore or chromophores is firstly calculated for a healthy zone of the skin on the basis of the value or values of the absorption coefficient for said healthy zone, and the concentration of the chromophore or chromophores is then calculated for the zone to be characterized on the basis of the concentration of the chromophore or chromophores for said healthy zone and of the value or values of the absorption coefficient for said zone to be characterized the or each chromophore is selected from the group consisting of: water, melanin, oxyhaemoglobin, deoxyhaemoglobin and bilirubin, the oxyhaemoglobin concentration and the deoxyhaemoglobin concentration are preferably calculated.

The object of the invention also relates to a computing system for calculation of a quantification indicator for quantifying the dermal reaction on the skin of a living being, such as a dermal reaction following the injection of an active ingredient, the skin having a plurality of chromophores, the system having the following a light source adapted for emitting an excitation light beam in order to illuminate a zone to be characterized on the skin, the skin reaction being included in said zone to be characterized, a spectrometer adapted for measuring the spectrum of a back scattered radiation coming from the skin as a result of the illumination of said zone to be characterized, an information processing unit having:

first determination means for determination, on the basis of the measured spectrum and for at least one given value of the wave length of the light beam, of a value for the absorption coefficient of the zone to be characterized, first calculation means for calculation, on the basis of the or each determined value of the absorption coefficient, of the concentration of at least one chromophore in the skin, and second calculation means for calculation of the quantification indicator for quantifying the dermal reaction on the basis of the previously calculated concentration of the or each chromophore, wherein the first determination means are further adapted for determining, on the basis of the measured spectrum and for at least one given value of the wave length of the light beam, a value for the absorption coefficient of the zone to be characterized, and wherein the second calculation means are adapted for calculating the quantification indicator for quantifying the dermal reaction also on the basis of the or each determined value of the diffusion coefficient.

BRIEF DESCRIPTION OF THE DRAWINGS

These characteristic features and advantages of the invention will become apparent upon reading the description which follows, provided purely by way of non limiting example, and with reference being made to the accompanying drawings, in which.

DETAILED DESCRIPTION

Figure 1:
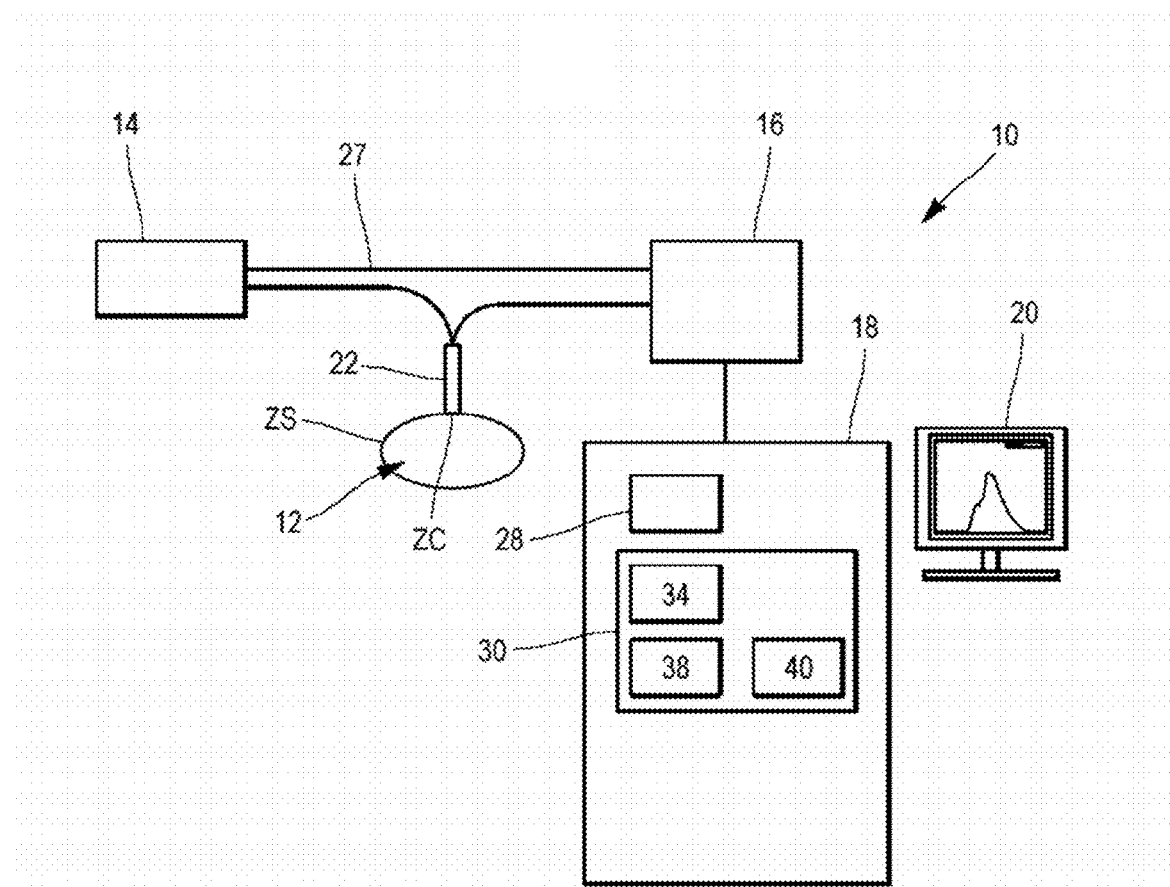
FIG. 1 is a highly schematic representation of a computing system for calculating a quantification indicator for quantifying a dermal reaction, the computing system comprising of a light source adapted for illuminating a zone the skin, a spectrometer adapted for measuring the spectrum of a back scattered radiation coming from the skin as a result of the illumination of said zone, and an information processing unit.

In FIG. 1, a computing system 10 is intended to be used for calculating an indicator IND for quantification of a dermal reaction on the skin 12 of a living being, such as a dermal reaction following the intradermal injection of an active ingredient for the implementation of a test for the presence of antibodies in the organism. The dermal reaction on the skin is also called skin reaction. The active ingredient is, for example, tuberculin for implementation of the test for tuberculosis. The quantification indicator IND is thus a function of the immune response.

Thus, in a general manner, the computing system 10 is designed for characterising, via the calculation of the quantification indicator IND, any skin reaction, in particular a colouring reaction, an inflammation reaction, an induration reaction, and even a skin alteration reaction.

The computing system 10 includes a light source 14 adapted for emitting a light beam for illuminating a zone to be characterized ZC on the skin 12, the skin reaction being included in said zone to be characterized ZC, and the light source additionally being adapted for illuminating a healthy zone ZS of the skin.

The computing system 10 includes a spectrometer 16 adapted for measuring the spectrum M of a back scattered radiation coming from the skin 12 as a result of the illumination of said zone to be characterized. The term back scattered radiation is understood to refer to the radiation passing through the skin 12 from a source zone corresponding to the zone of the epidermis illuminated by the light beam emitted from the light source 14, and detected in a detection zone at a given distance from the source zone, the most likely paths of the photons detected at said given distance from the source zone being in the shape of a banana. The person skilled in the art will thus observe that the farther away the detection zone is from the source zone, the deeper into the skin 12 the photons would have travelled, and the lower the likelihood of them re-emerging in large numbers at this spot taken into consideration the absorption of photons by the skin 12.

Figure 8:
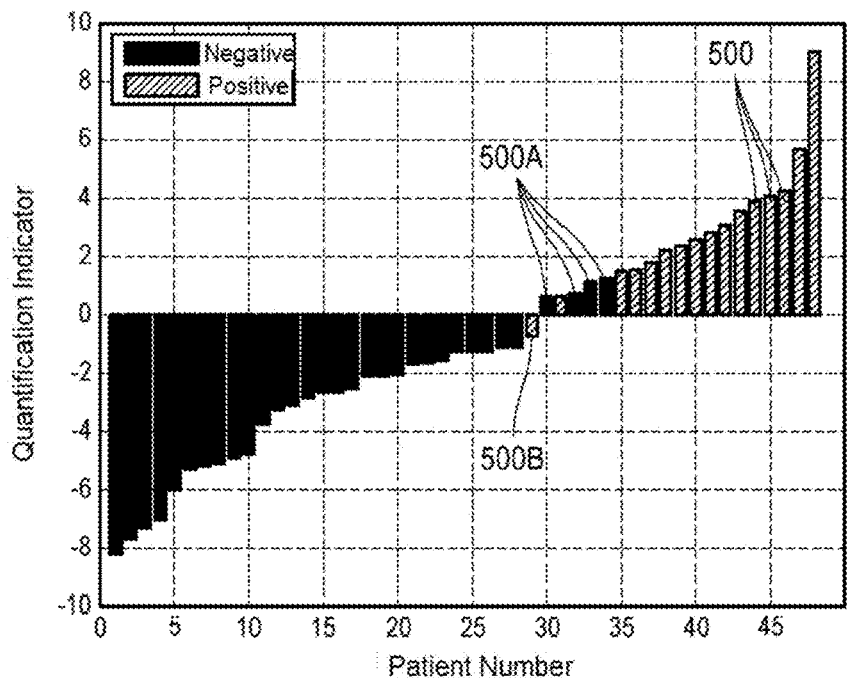
FIGS. 8 and 9 are views that are similar to that of FIG. 7 by implementing a method according to an example of the invention, respectively according to a further example of the invention.
Figure 9:
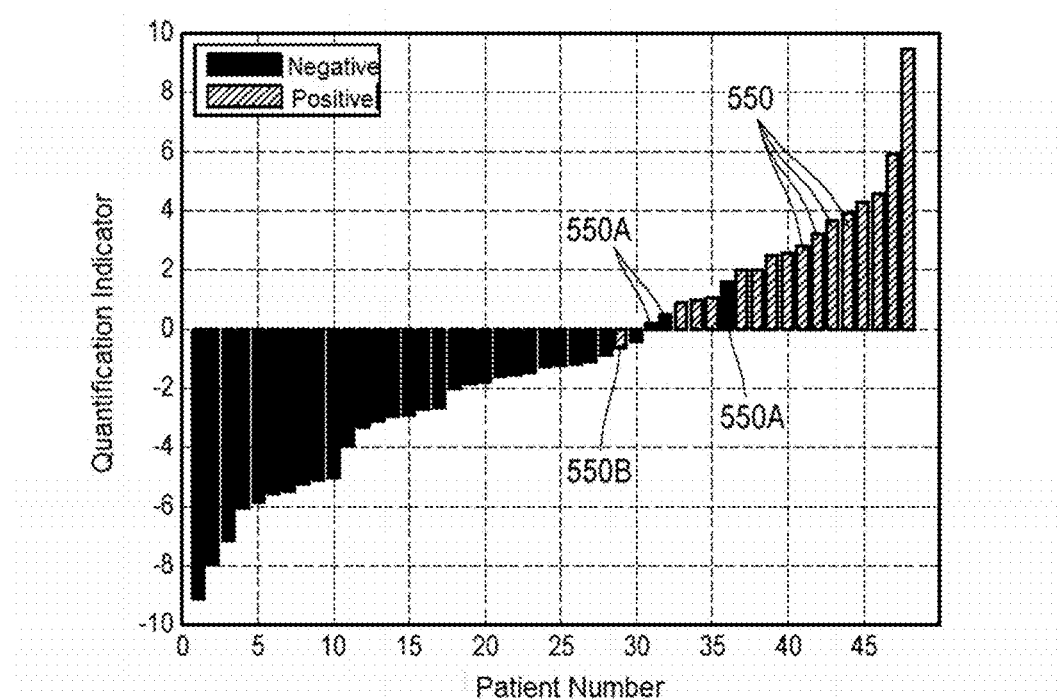

The computing system 10 includes an information processing unit 18 and a screen 20 for displaying various quantification indicators IND calculated for various different living beings, these calculated indicators being for example represented in the form of histograms, visible in FIGS. 8 and 9.

Figure 2:
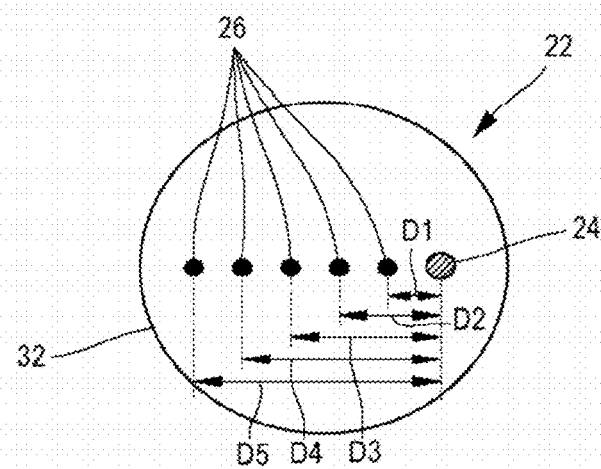
FIG. 2 is a schematic representation of an end of a probe intended to be in contact with the skin, the probe comprising an excitation optical fibre for conveying the light beam coming from the light source and a plurality of detection optical fibres for conveying to the spectrometer the radiation back scattered by the skin.

In addition, the computing system 10 includes a probe 22 meant to be positioned in contact with the skin 12 and including, as shown in FIG. 2, at least one excitation optical fibre 24 for conveying the light beam from the source 14 to the skin 12, and a plurality of detection optical fibres 26, each detection optical fibre 26 being adapted for conveying to the spectrometer 16, a part of the radiation back scattered by the skin 12. Advantageously, the detection fibres 26 are arranged in concentric rings and the excitation fibre 24 is disposed at the center of said rings. Thus, there are several detection fibres 26 available for a same given distance Di with the excitation fibre 24. The signals measured for a same given distance Di are then averaged, which makes it possible to increase the signal to noise ratio.

The skin 12 includes, as known per se, a plurality of chromophores, such as in particular melanin, oxyhaemoglobin, also denoted as $HbO_2$, deoxyhaemoglobin also denoted as Hb, water and bilirubin.

The skin 12 is, for example, the skin of a patient, as will be described later in the example shown in FIGS. 8 and 9. By way of a variant, the skin 12 is the skin of an animal, such as a mammal, with tests having also been carried out by way of example on the skin of a pig.

The light source 14, shown in FIG. 1, is adapted for emitting a light beam of wave length $\lambda$, the values of the wave length $\lambda$ being preferably comprised between 400 nm and 1000 nm. In other words, the light source 14 is adapted for emitting a beam of white light and near infrared light beam.

Additionally, in the example shown in FIG. 1, the light source 14 is also connected directly to the spectrometer 16 by means of a direct link optical fibre 27, also known as excitation return. This configuration, which is optional, provides the ability to more precisely take into consideration the spectrum of emission, as well as its potential fluctuations, and thereby to improve the reliability of the result.

The spectrometer 16 is coupled to the detection optical fibres 26, for example by means of a translation stage, not shown, that allows for the multiplexing of all the detection fibres 26 over a single spectrometer. The spectrometer 16 is, for example, a fibre spectrometer. By way of a variant, a multi-channel spectrometer is used. In a general manner, the spectrometer 16 is adapted to produce a signal over various different determined ranges of wave lengths. This may involve for example a series of optical sensor detectors, such as photodiodes, each detector being associated with a specific wave length range.

The information processing unit 18 includes a data processor 28 and a memory 30 associated with the processor.

The probe 22 includes a protective casing 32 for the protection of the optical fibres 24, 26, the external diameter of the protective casing 30 is for example of the order of 6 mm. The probe 22 includes, for example, one single excitation fibre 24 and forty-two detection fibres 26. More specifically, the detection fibres 26 are arranged in concentric rings 6, each ring including seven fibres.

The excitation fibre 24 has, for example, a diameter of the order of 500 μm (microns), and each detection fibre 26 has, for example, a diameter of the order of 300 μm.

The detection optical fibres 26 are preferably positioned at different distances Di from the excitation optical fibre 24, where i is the index of the distance, i being an integer varying between 1 and N, where N is the number of distinct predetermined distances. By way of example in FIG. 2, the probe 22 includes five detection fibres 26 respectively positioned at distances $D_1$, $D_2$, $D_3$, $D_4$ and $D_5$. By convention, it will be assumed that the smaller the value of the index i, the shorter will be the associated distance Di.

In addition, not shown, the forty-two detection fibres 26 are divided into six groups of seven detection fibres 26 positioned at six respective distances $D_1$, $D_2$, $D_3$, $D_4$, $D_5$ and $D_6$ from the excitation fibre 24. All the detection fibres 26 of a same given group are positioned at a same given distance $D_i$ from the excitation fibre 24.

The light beam capable of passing through the excitation return 27 so as to be received by the spectrometer 16 is a light beam having an attenuated intensity value as compared to that of the radiation incident on the skin, in order to avoid a glare from the spectrometer 16. In the example described, an excitation beam is formed of 18 excitation optical fibres 24, while the excitation return 27 is formed of one single fibre. Thus, the excitation return signal sent to the spectrometer 16 has an intensity that is attenuated as compared to the excitation signal, the attenuation resulting from the fact that the excitation return 27 is formed of one single optical fibre whereas 18 excitation fibres 24 constitute the excitation beam.

The memory 30 is adapted to store a first software 34 for determination, on the basis of the measured spectrum M and for at least one given value of the wave length λ of the light beam, of a value for the absorption coefficient $\mu_a$ of the corresponding zone ZC, ZS of the skin 12. The first determination software 34 is also adapted for determining, on the basis of the measured spectrum M and for at least one given value of the wave length λ of the light beam, a value for the diffusion coefficient $\mu_s$ of the corresponding zone ZC, ZS of the skin 12.

The inventors deemed that it was important to consider the absorption coefficient $\mu_a$ and the diffusion coefficient $\mu_s$ as variables of different types, given that diffusion is not comparable to absorption. In fact, in contrast to the state of the art, it would be inaccurate to equate the diffusion coefficient $\mu_s$ to a chromophore, whose concentration is determined on the basis of the value of the attenuation. In other words, diffusion is not a component of absorption. Rigorous consideration being taken of diffusion in a diffusion medium instead assumes absorption and diffusion to be considered as different phenomena. It is then possible to simultaneously estimate a value for the absorption coefficient $\mu_a$ and a value for the diffusion coefficient $\mu_s$ in order to characterise the propagation of light in the medium, such estimations being performed on the basis of the measurement of the light back scattered by the tissue.

The term diffusion coefficient represents in an interchangeable manner the reduced diffusion coefficient, denoted by $\mu_s'$, and the diffusion coefficient, denoted by $\mu_s$, it being known that these two values are related by the equation:

$$\mu_s' = \mu_s \times (1-g)$$

g designating the anisotropy coefficient, the latter being assumed to be constant and equal to 0.8 in biological tissues.

Hereinafter in the text, these values are referred to by the term diffusion coefficient, using the notation $\mu_s$.

The memory 30 is suitable for storing a first software 38 for calculation, on the basis of the or each determined value of the absorption coefficient $\mu_a$, of the concentration of at least one chromophore in the skin 12.

The memory 30 is also suitable for storing a second software 40 for calculation of the indicator IND for quantification of the dermal reaction on the basis of the previously calculated concentration of the or each chromophore and also on the basis of the or each determined value of the diffusion coefficient $\mu_s$.

Alternatively, the second calculation software 40 is adapted for calculating the quantification indicator IND on the basis of a difference between the concentrations of the or each chromophore Hb, $HbO_2$ of the healthy zone ZS and of the zone to be characterized ZC and on the basis of the difference or differences between the determined values of the diffusion coefficient $\mu_s$ of the healthy zone ZS and the zone to be characterized ZC.

Figure 3:
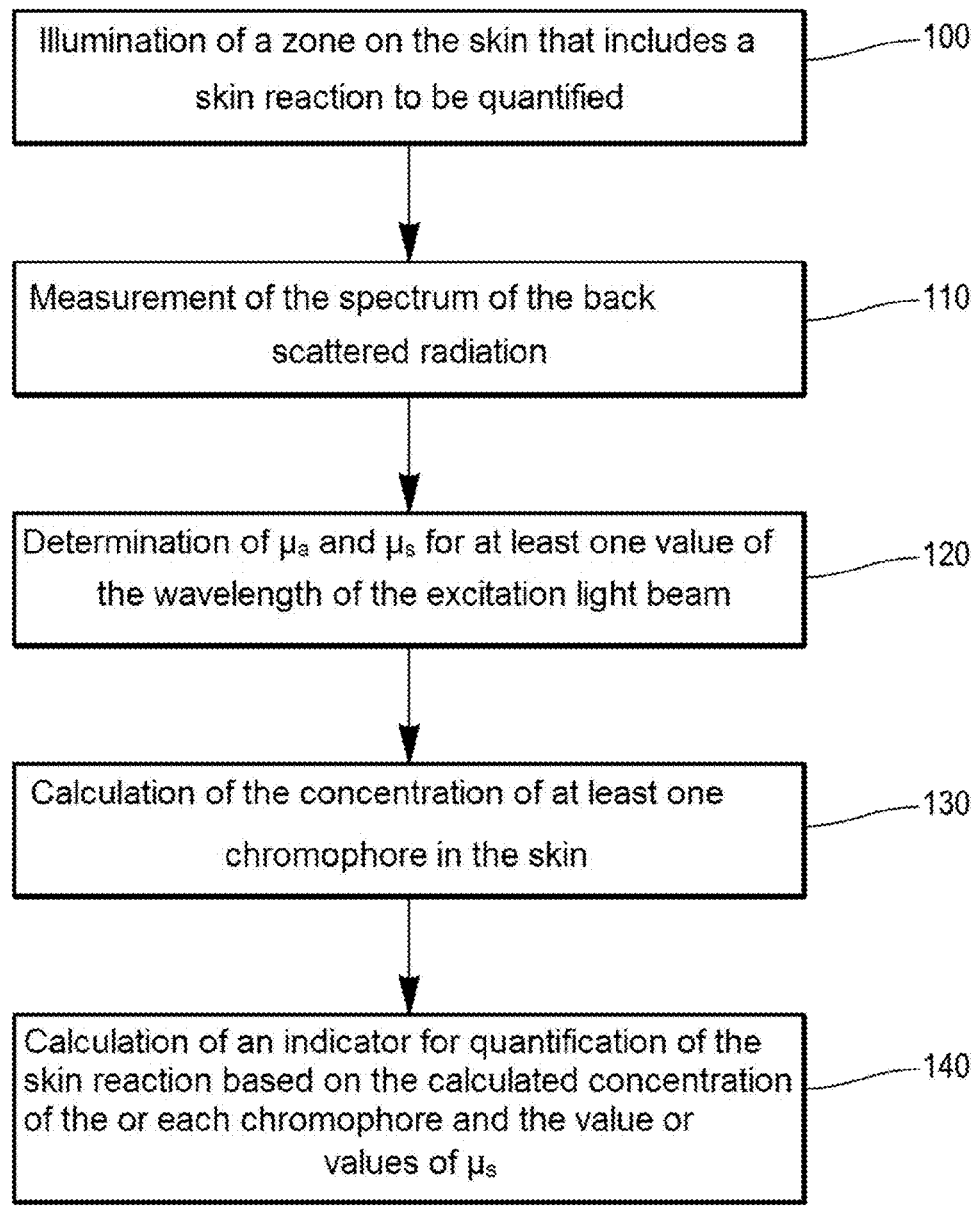
FIG. 3 is a flowchart of a calculation method according to the invention.

The operation of the computing system 10 according to the invention will now be described with the aid of the flowchart shown in FIG. 3 illustrating a method for calculation according to the invention of the indicator IND for quantification of the skin reaction.

During the initial step 100, the corresponding zone ZC, ZS of the skin 12 is first of all illuminated by means of the light source 14 for a given value of the wave length λ of the light beam. In order to do this, an operator places the probe 22 in contact with the corresponding zone ZC, ZS of the skin 12, in a manner such that the excitation fibre 24 and the detection fibres 26 are facing said corresponding zone ZC, ZS.

The spectrum M of the back scattered radiation coming from the skin 12 as a result of the illumination of said corresponding zone ZC, ZS is measured for said given value of the wave length λ of the light beam and with the use of the spectrometer 16 during the subsequent step 110.

The steps 100 and 110 are repeated automatically by the computing system 10 by varying the wave length λ of the light beam within a predetermined range. The predetermined range of values of the wave length λ of the light beam is, for example, the range between 400 nm and 1000 nm, preferably the range between 450 nm and 900 nm, more preferably the range between 450 nm and 800 nm. The interval between two successive values of the wave length λ, also known as sampling interval, is, for example, equal to 1 nm, preferably equal to 0.5 nm, and even more preferably equal to 0.33 nm.

In a general manner, the minimum number of values of the wave length λ to be considered corresponds to the number of chromophores considered. It will be appreciated that the higher the number of values of the wave length λ, the greater will be the accuracy of the final indicator.

The duration of the phase corresponding to all of the steps 100 and 110 repeated for the plurality of values of the wave length λ, also referred to as acquisition phase, is less than about ten seconds for the corresponding zone ZC, ZS. This duration is quite likely to be even shorter depending on the predetermined range of values of the wave length λ and the selected value of the sampling interval, it being understood that the greater the value of the sampling interval, the shorter will be the duration of the acquisition phase.

The measured spectrum M, that is to say, the spectrum of the back scattered signal, satisfies the general equation:

$$M = S \times R \times G \times D \tag{1}$$

where S represents the intensity of the light source 14,

R represents the reflectance corresponding to the diffusion of the light in the skin tissue 12, G represents the efficiency of collection at the probe 22 in contact with the skin 12, with 0<U<1, and D represents the response of the spectrometer 16.

When the values of the intensity S of the source, of the collection efficiency G and the response D of the spectrometer are known, then the value of the reflectance R is obtained directly with the use of the measured spectrum M and for each value of the wave length λ according to the equation (1).

According to a first variant, when the values of the intensity S of the source and of the response D of the spectrometer are not known, a calibration measurement is carried out prior to the steps 100 and 110 on a reference sample, also referred to as ghost.

The measured spectrum for the ghost is then denoted by $M_{std}$ and satisfies the following equation:

$$M_{std} = S \times R_{std} \times G_{std} \times D \tag{2}$$

The measured spectrum for the skin 12 is then denoted by $M_{skin}$ and satisfies the following equation:

$$M_{skin} = S \times R_{skin} \times G_{skin} \times D \tag{3}$$

A first ratio B of the measured spectrum for the skin 12 over the measured spectrum for the ghost is then calculated, and provides the ability to determine the reflectance $R_{skin}$ of the skin 12 while being rid of the values of the intensity S of the source and the response R of the spectrometer, according to the following equations:

$$B = \frac{M_{skin}}{M_{std}} = \frac{S \times R_{skin} \times G_{skin} \times D}{S \times R_{std} \times G_{std} \times D} = \frac{R_{skin} \times G_{skin}}{R_{std} \times G_{std}} \tag{4}$$

$$R_{skin} = B \times R_{std} \times \frac{G_{std}}{G_{skin}} \tag{5}$$

and then $R_{skin} = B \times R_{std}$ (6)

by considering moreover that the collection efficiency $G_{skin}$ when the spectrum is measured for the skin 12 is substantially equal to the collection efficiency $G_{std}$ when the spectrum is measured for the ghost.

According to a second variant, when the values of the intensity S of the source and the response R of the spectrometer are not known, a pre-treatment measurement is carried out with the aid of the excitation return 27, and satisfies the following equation:

$$M_{direct} = S \times G_{direct} \times D \times k \tag{7}$$

where k represents the coefficient of attenuation of the intensity in the optical fibre corresponding to the excitation return 27 as compared to that in the detection fibres 26.

A second ratio C of the measured spectrum for the skin 12 over the spectrum measured directly via the excitation return 27 is then calculated, and provides the ability to determine the reflectance $R_{skin}$ of the skin 12 while being rid of the values of the intensity S of the source and the response R of the spectrometer, according to the following equations:

$$C = \frac{M_{skin}}{M_{direct}} = \frac{S \times R_{skin} \times G_{skin} \times D}{S \times G_{direct} \times k} = \frac{R_{skin} \times G_{skin}}{G_{std} \times k} \tag{8}$$

$$R_{skin} = C \times k \times \frac{G_{direct}}{G_{skin}} \tag{9}$$

and then $R_{skin} = C \times k$ (10)

by considering in addition that the collection efficiency $G_{skin}$ when the spectrum is measured for the skin 12 is substantially equal to the collection efficiency $G_{direct}$ when the spectrum is measured directly via the excitation return 27.

Thus, in a general manner, based on a measurement M(λ) of the back scattered light at a given wave length λ, the reflectance R(λ) of the tissue examined at this same wave length λ is determined. The influence of the light source 14 and the spectrometer 16 used may thus be averted. The reflectance corresponds to the response of the tissue to an excitation light, based on its properties of absorption and diffusion.

Figure 4:
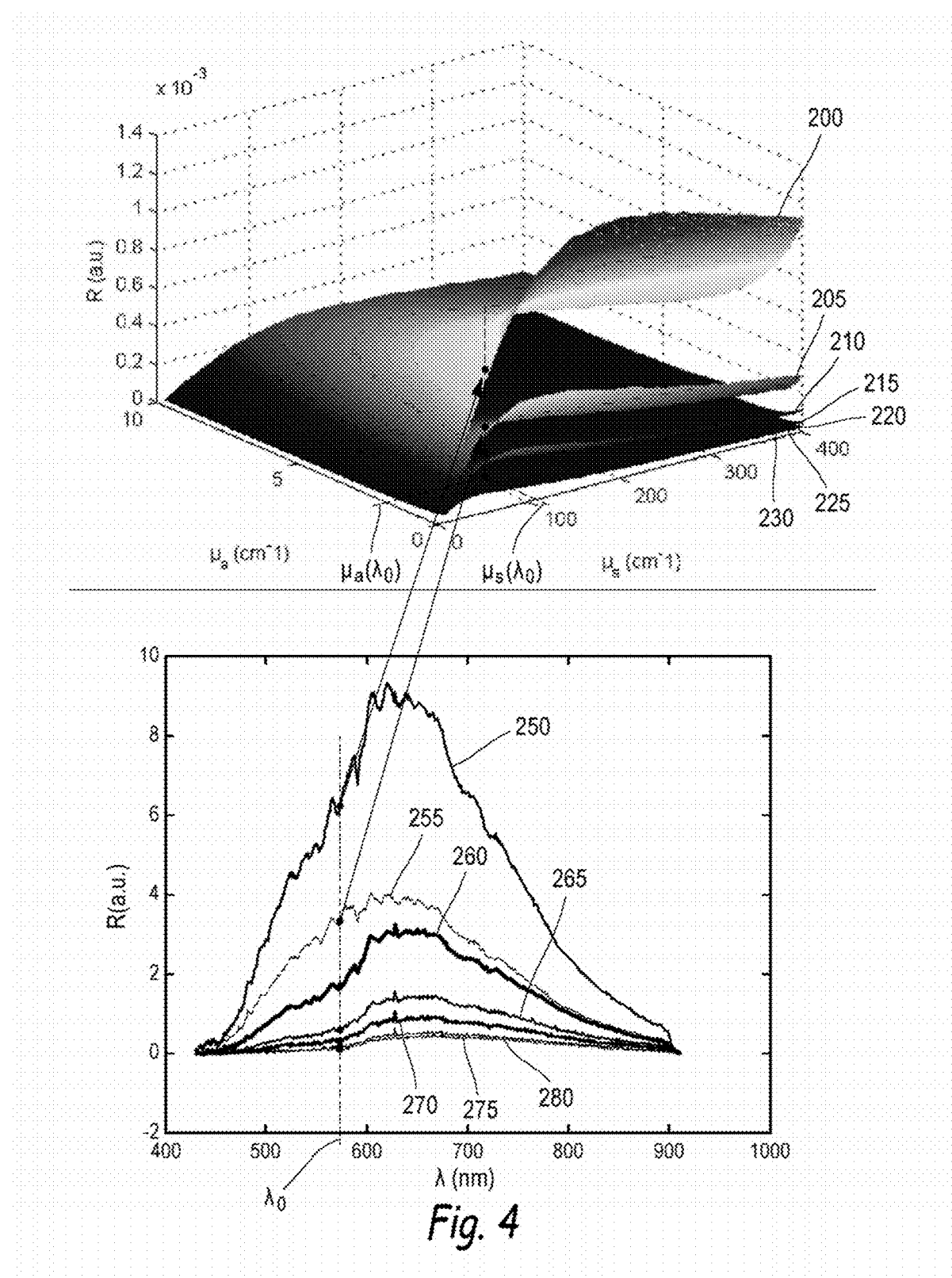
FIG. 4 is a set of surfaces representing the reflectance as a function of the absorption coefficient and the diffusion coefficient, each surface corresponding to a respective distance between the excitation fibre and the corresponding detection fibre, and a set of curves representing the reflectance as a function of the wave length of the incident light beam, each curve corresponding to said respective distance.

In addition, when the computing system 10 includes a plurality of detection optical fibres 26 disposed at various different predetermined distances $D_i$ from the excitation optical fibre 24, the reflectance R is calculated for the plurality of values of the wave length λ, and for each of said predetermined distances $D_i$, as represented in FIG. 4.

In FIG. 4, the curves 250, 260, 265, 270, 275 and 280 thus correspond to the reflectance R obtained for six distinct predetermined distances $D_i$, based on measurements M, with the relationship between measurement and reflectance being obtained as previously described. The curve 250 corresponds to the reflectance R at the smallest distance $D_1$ amongst said distances $D_i$, and the curve 280 corresponds to the reflectance R calculated at the largest distance $D_N$ amongst said distances D. The curve 255 corresponds to the reflectance R obtained for the excitation return 27. It is thus observed that the greater the distance $D_i$ between the excitation fibre 24 and the corresponding detection fibre 26, the lower is the amplitude of the reflectance R. This is due to the fact that the photons would have traveled deeper into the skin 12, and therefore there would be a lower number of them likely to re-emerge at the distance $D_N$ from the excitation fibre 24 taking into account the absorption of the photons by the skin 12.

The inventors have found that results which are practically useful are obtained by way of implementing the detection fibres arranged according to four distances, with the proviso that the maximum distance $D_N$ be at least 2 mm.

At the completion of the acquisition phase corresponding to all of the steps 100 and 110 repeated for the plurality of values of the wave length λ, a value for the absorption coefficient $\mu_a$ and a value for the diffusion coefficient $\mu_s$ of the corresponding zone ZC, ZS are determined, during the step 120 by means of using the first determination software 34 for at least one value of the wave length λ of the excitation light beam and on the basis of the measured spectrum M. In particular, the values for the absorption coefficient $\mu_a$ and the diffusion coefficient $\mu_s$ of the corresponding zone ZC, ZS are determined by making use of the previously determined reflectance R.

In the described example, the values for the absorption coefficient $\mu_a$ and the diffusion coefficient $\mu_s$ of the corresponding zone ZC, ZS are determined for each of the values of the wave length λ previously used during the steps 100 and 110, and the values for the absorption coefficient $\mu_a$ and the diffusion coefficient $\mu_s$ are then respectively denoted by $\mu_a(\lambda)$ and $\mu_s(\lambda)$.

In addition, when the computing system 10 includes a plurality of detection optical fibres 26 disposed at various different predetermined distances $D_i$ from the excitation optical fibre 24, the values of the absorption coefficient $\mu_a(\lambda)$ and the diffusion coefficient $\mu_s(\lambda)$ are determined based on the spectra M measured for each of said predetermined distances D. In particular, the values of the absorption coefficient $\mu_a(\lambda)$ and the diffusion coefficient $\mu_s(\lambda)$ of the corresponding zone ZC, ZS are determined by making use of the reflectance R determined on the basis of each spectrum measured for each of said predetermined distances $D_i$.

Still additionally, a reference table LUT also called Look Up Table is predetermined before the step of determination 120, for example prior to the steps 100 and 110. The Look Up Table LUT includes a plurality of values for the reflectance of the skin 12, each value of said LUT being predetermined for a respective pair of values for the absorption coefficient $\mu_a$ and the diffusion coefficient $\mu_s$. The predetermination of the Look Up Table LUT is carried out, for example, by making use of a digital simulation means of the Monte Carlo type.

Alternatively, the Look Up Table LUT is determined analytically, for example according to the method described in article by Farrell et al, entitled "A diffusion theory model of spatially resolved, steady-state diffuse reflectance for the non-invasive determination of tissue optical properties in vivo", published in *Medical Physics* in 1992. The reflectance R is then described as a function of: the coefficients of absorption $\mu_a$ and reduced diffusion $\mu_s$, of the skin 12, the distance $D_i$ between the excitation fibres 24 and detection fibres 26, also denoted by r; and the refractive index of the medium n, according to the following equation:

$$R = f(\mu_a, \mu_s, r, n) \tag{11}$$

The refractive index n is, for example, considered equal to 1.36, which corresponds to a mean index for biological tissues.

A parameter A relative to the reflections at the interfaces and dependent upon the refractive indices of the ambient medium $n_{ambient}$ and of the tissues $n_{tissues}$ then makes it possible to process boundary conditions in accordance with the following equations:

$$A = [1 + r_i]/[1 - r_i] \tag{12}$$

$$r_i = 1.440 n_r^{-2} + 0.710 n_r^{-1} + 0.0636 n_r + 0.668 \tag{13}$$

$$n_r = n_{tissues}/n_{ambient} \tag{14}$$

The person skilled in the art will appreciate that if the ambient medium is air, then $n_r$ is equal to $n_{tissues}$.

The reflectance is thus calculated as being the density of current given by the diffusion equation, perpendicular to the output surface with r equals to 0.

In Posing:

$$z_0 = \frac{1}{\mu_a + \mu_s'} \tag{15}$$

$$\mu_{eff} = \sqrt{3\mu_a(\mu_a + \mu_s')}$$

the following is thus obtained:

$$R = \frac{z_0}{4\pi} \times \left[\left(\mu_{eff} + \frac{1}{r_1}\right)\frac{e^{-\mu_{eff} r_1}}{r_1^2} + \left(1 + \frac{4}{3}A\right)\left(\mu_{eff} + \frac{1}{r_2}\right)\frac{e^{-\mu_{eff} r_2}}{r_2^2}\right]$$

with:

$$r_1 = \sqrt{z_0^2 + r^2} \tag{16}$$

$$r_2 = \sqrt{z_0^2\left(1 + \frac{4}{3}A\right)^2 + r^2}$$

By convention, the reflectance thus predetermined is then denoted by $R_{LUT}$, the reflectance measured during the steps 100 and 110 being thus denoted by $R_{measurement}$.

In addition, the measurements are then processed in order to make them comparable to the values of the Look Up Table LUT. The reflectance curve to be compared to the database is calculated as follows. For a given wave length λ: $R_{ref-LUT}$ corresponds to the reflectance curve calculated by the Monte Carlo programme for the optical parameters of the reference ghost, these parameters being always known. $R_{ref-measurement}$ corresponds to the measurement performed on the ghost. Finally, $R_{measurement}$ is the reflectance measured for the corresponding zone ZC, ZS. A readjusted reflectance, denoted by $R_{unknown-LUT}$, is then obtained by making use of the following equation:

$$R_{unknown-LUT} = R_{measurement} \times [R_{ref-LUT}/R_{ref-measurement}] \tag{17}$$

In a similar manner, when the computing system 10 includes a plurality of detection optical fibres 26 disposed at various different predetermined distances $D_i$, from the excitation optical fibre 24, the predetermination of the Look Up reference table LUT is carried out for each of said predetermined distances $D_i$, each value of said table LUT being predetermined for a respective pair of values of the absorption coefficient and the diffusion coefficient and for said different distances $D_i$, as shown in FIG. 4. By convention, the reflectance thus predetermined is then denoted by $R_{LUT}^{Di}$ for each respective distance $D_i$, with the reflectance measured during the steps 100 and 110 being then denoted by $R_{measurement}^{Di}$ for each respective distance $D_i$.

In FIG. 4, the sheets 200, 205, 210, 215, 220 and 225 thus correspond to the reflectances $R_{LUT,Di}$ predetermined for the six distinct predetermined distances $D_i$, with the sheet 200 corresponding to reflectance $R_{LUT,D1}$ predetermined for the smallest distance $D_1$ from amongst said distances $D_i$, and the sheet 225 corresponding to the reflectance $R_{LUT,DN}$ predetermined for the greatest distance $D_N$ from amongst said distances $D_i$. It is then also observed that the greater the distance between the excitation fibre 24 and the corresponding detection fibre 26, the lower is the amplitude of the reflectance R. The sheet 230 corresponds to the reflectance R obtained for the excitation return 27.

During the determination step 120, the pair of determined values for the absorption coefficient $\mu_a$ and the diffusion coefficient $\mu_s$ is then the one that minimises the error between the predetermined reflectances $R_{LUT}$ of the Look Up reference table LUT and the value or values of reflectance $R_{measurement}$ measured for a given value of the wave length $\lambda$.

The pair of determined values for the absorption coefficient $\mu_a$ and the diffusion coefficient $\mu_s$ satisfies, for example, the following equation:

$$(\mu_a, \mu_s) = \mathrm{Argmin}_{(\mu_a,\mu_s)} \sqrt{\sum_{i=1}^{N} \left(R_{LUT}^{D_i} - R_{measurement}^{D_i}\right)^2} \quad (18)$$

FIG. 4 illustrates by way of an example the determination of the pair $(\mu_a, \mu_s)$ obtained for the wave length value $\lambda_o$, this latter then being denoted by $(\mu_a(\lambda_0), \mu_s(\lambda_0))$.

This determination step 120 is repeated for each of the values of the wave length $\lambda$ in the range and based on the predetermined sampling interval, in accordance with the values described here above.

The concentration of at least one chromophore in the skin is then calculated, during step 130, on the basis of the or each determined value of the absorption coefficient $\mu_a(\lambda)$ and by making use of the first calculation software 38.

The absorption coefficient $\mu_a(\lambda)$ satisfies the following equation:

$$\mu_a(\lambda) = Deox\mu_{ahb}(\lambda) + Ox\mu_{ahbO2}(\lambda) + W\mu_{aeau}(\lambda) + Bil\mu_{aBil}(\lambda) + Fat\mu_{aFat}(\lambda) + L_{epi}/L_{derm}*Mel\mu_{aMel}(\lambda) \quad (19)$$

where Deox represents the deoxyhaemoglobin concentration in the corresponding zone ZC, ZS of the skin 12, Ox represents the concentration of oxyhaemoglobin in said zone of skin 12, W represents the concentration of water in said zone of skin 12, Bil represents the concentration of bilirubin in said zone of the skin 12, Fat represents the concentration of fat in said zone of skin 12, and Mel represents the fraction of melanosomes present in an epidermal layer of thickness $L_{epi}$ assumed to be equal to 60 µm for a total thickness of the dermis $L_{derm}$ assumed to be equal to 1.5 mm.

It is specified that the terms $\mu_{ahb}(\lambda)$, $\mu_{ahbO2}(\lambda)$, $\mu_{awater}(\lambda)$, $\mu_{aBil}(\lambda)$, $\mu_{aFat}(\lambda)$ and $\mu_{aMel}(\lambda)$ respectively represent the coefficients of absorption for deoxyhaemoglobin, oxyhaemoglobin, water, bilirubin and fat for a unit concentration.

The or each chromophore is selected from among the group consisting of: water, melanin, oxyhaemoglobin, deoxyhaemoglobin and bilirubin, with the oxyhaemoglobin $HbO_2$ concentration and the deoxyhaemoglobin Hb concentration preferably being calculated.

The concentrations of bilirubin Bil and fat Fat are, for example, not taken into consideration, the quantities $Bil.\mu_{aBil}$ and $Fat.\mu_{aFat}$ being assumed to be negligible for the values of the wave length $\lambda$ between 400 nm and 1000 nm. In other words, it is deemed that the contribution of bilirubin and fat to absorption is negligible as compared to the other chromophores for this range of values of the wave length $\lambda$, for the dermal reaction studied.

In addition, during step 130 for calculating the concentration of the chromophore or chromophores $HbO_2$, Hb, the concentration of the chromophore or chromophores $HbO_2$, Hb is first calculated for the healthy zone ZS of the skin 12, visible in FIG. 1, on the basis of the value or values of the absorption coefficient $\mu_a$ of said healthy zone ZS, and the concentration of the chromophore or chromophores $HbO_2$, Hb is then calculated for the zone to be characterized ZC on the basis of the concentration of the chromophore or chromophores for the healthy zone ZS and the value or values of the absorption coefficient $\mu_s$ of said zone to be characterized ZC.

Figure 5:
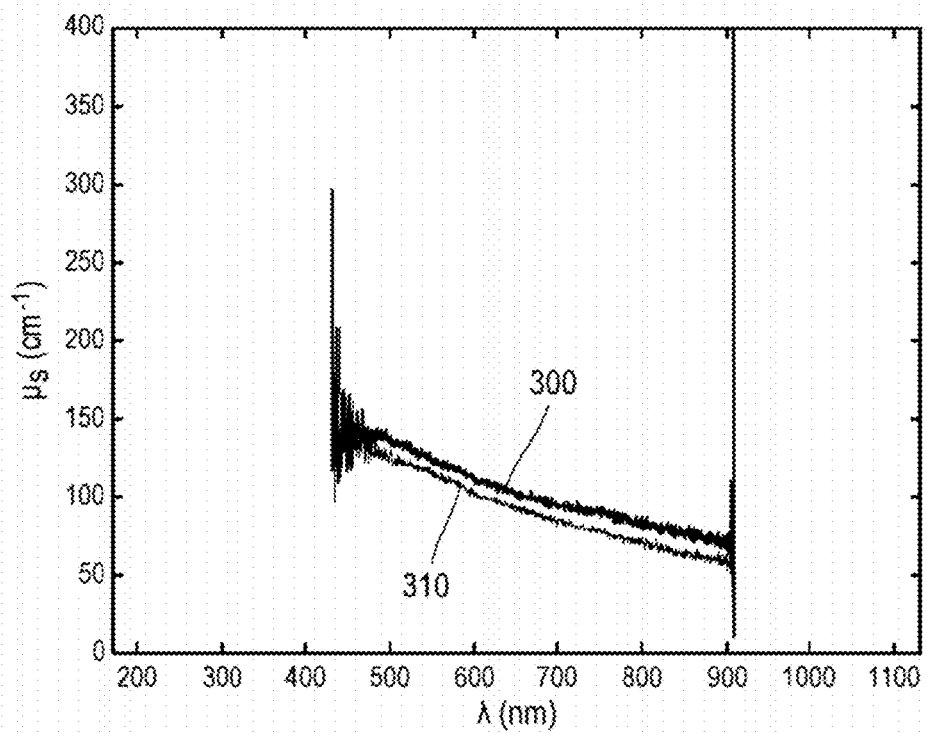
FIG. 5 is a set of curves representing the diffusion coefficient as a function of the wave length of the incident light beam, for a healthy zone of the skin, and respectively for a zone to be characterized that has a skin reaction.

On FIG. 5, the curve 300 represents the values applied for the diffusion coefficient $\mu_s$ of the healthy zone ZS for the values of the wave length $\lambda$ between 400 nm and 900 nm, and the curve 310 represents the values applied for the diffusion coefficient $\mu_s$ of the zone to be characterized ZC for the same range of values of the wave length $\lambda$.

Figure 6:
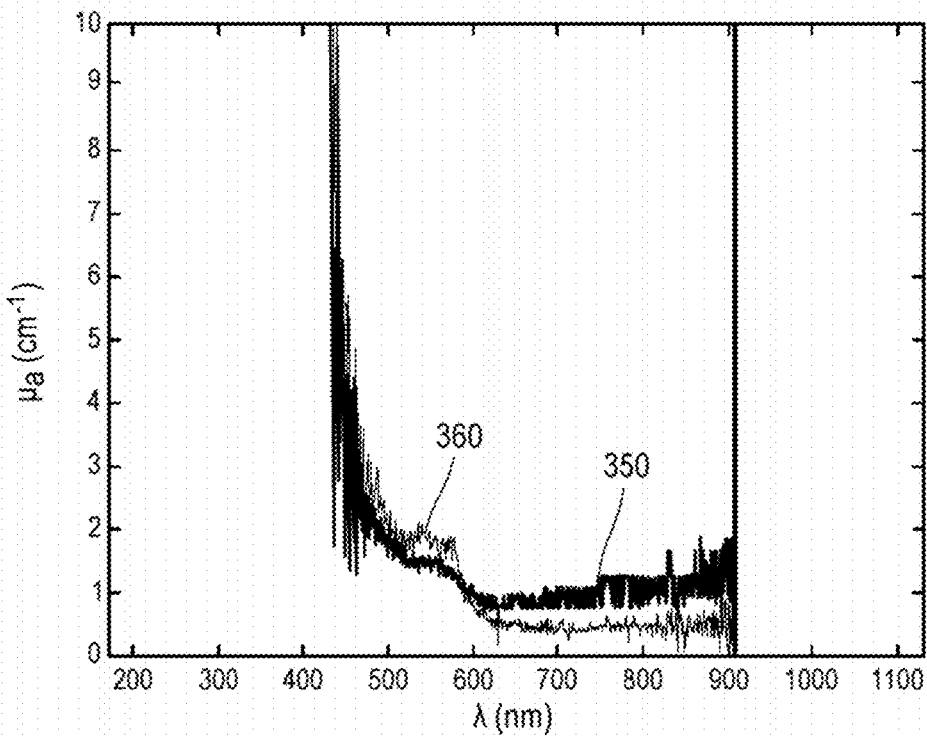
FIG. 6 is a set of curves representing the absorption coefficient as a function of the wave length of the incident light beam, for a healthy zone of the skin, and respectively for a zone to be characterized that has a skin reaction.

In FIG. 6, the curve 350 represents the values applied for the absorption coefficient $\mu_a$ of the healthy zone ZS for the values of the wave length $\lambda$ between 400 nm and 900 nm, and the curve 360 represents the values applied for the absorption coefficient $\mu_a$ of the zone to be characterized ZC for the same range of values of the wave length $\lambda$.

According to this additional aspect, the steps 100, 110 and 120 previously described above are then carried out during an initial period for the healthy zone ZS, then during a subsequent period for the zone to be characterized ZC.

The oxyhaemoglobin concentration $HbO_2$, the deoxyhaemoglobin concentration Hb, the melanin concentration Mel and the concentration of water W, are firstly calculated by making use of the first calculation software 38, for the healthy zone ZS based on the values of the absorption coefficient $\mu_a$ of said healthy zone ZS and the initial standard values of the oxyhaemoglobin concentration $HbO_2$, the deoxyhaemoglobin concentration Hb, the melanin concentration Mel and the concentration of water W. These standard values are for example derived from the literature.

By assuming that the value $Mel.\mu_{aMel}$ does not vary between the healthy zone ZS and the zone to be characterized ZC, the oxyhaemoglobin concentration $HbO_2$ and the deoxyhaemoglobin concentration Hb are then calculated by making use of the first calculation software 38, for the zone to be characterized ZC based on the values of the absorption coefficient $\mu_a$ of said zone to be characterized ZC and initial values of the concentrations equal to the most recent values previously calculated for the healthy zone ZS. The initialisation of the algorithm using values derived from the healthy zone ZS provides for more appropriately taking into consideration the phototype of the individual.

The quantification indicator IND for quantifying the skin reaction is finally calculated, during step 140, by making use of the second calculation software 40 and on the basis of the concentration of the or each chromophore $HbO_2$, Hb previously calculated and on the basis also of the or each determined value of the diffusion coefficient $\mu_s$ of the zone to be characterized ZC.

The quantification indicator IND is preferably calculated based on an average, such as the arithmetic mean, of a plurality of values of the diffusion coefficient $\mu_s$ of the zone to be characterized ZC, these values of the diffusion coefficient $\mu_s$ being determined for a plurality of values of the wave length $\lambda$, for example, comprised between 450 nm and 800 nm, preferably between 650 nm and 800 nm, even more preferably between 740 nm and 760 nm.

The quantification indicator IND then satisfies, for example, the following equation:

$$IND = \alpha_1 + \beta_1 \times Ox + \gamma_1 \times Deox + \delta_1 \times Dif \quad (20)$$

where IND represents the quantification indicator for quantifying the dermal reaction, $\alpha_1$, $\beta_1$, $\gamma_1$ and $\delta_1$ are predetermined coefficients for a given value of the time period between the moment of measurement of the spectrum M of the back scattered radiation and the moment of injection of the active ingredient, with $\beta_1$, $\gamma_1$ and $\delta_1$ having non-null values, Dif represents the average, such as the arithmetic mean, of the determined value or values of the diffusion coefficient $\mu_s$ calculated for the wave length ranges indicated here above, that is [450 nm; 800 nm], preferably [650 nm; 800 nm], and even more preferably [740 nm; 760 nm].

The values of the coefficients $\alpha_1$, $\beta_1$, $\gamma_1$ and $\delta_1$ are, for example, predetermined in an empirical manner based on tests performed on a set of patients. This predetermination is done preferably via a discriminant factor analysis. By way of a variant, the predetermination is done via a principal component analysis.

Alternatively, the quantification indicator IND is computed based on a difference between the concentrations of the or each chromophore Hb, HbO$_2$ of the healthy zone ZS and the zone to be characterized ZC and on the basis of the difference or differences between the determined values of the diffusion coefficient $\mu_s$ of the healthy zone ZS and the zone to be characterized ZC.

According to this variant, the quantification indicator IND then satisfies, for example, the following equation:

$$IND = \alpha'_1 + \beta'_1 \times \Delta Ox + \gamma'_1 \times \Delta Deox + \delta'_1 \times \Delta Dif \quad (21)$$

where IND represents the quantification indicator for quantifying the dermal reaction, $\alpha'_1$, $\beta'_1$, $\gamma'_1$ and $\delta'_1$ are predetermined coefficients for a given value of the time period between the moment of measurement of the spectrum M of the back scattered radiation and the moment of injection of the active ingredient, with $\beta'_1$, $\gamma'_1$ and $\delta'_1$ having non-null values $\Delta Ox$ and $\Delta Deox$ represent a difference between the oxyhaemoglobin concentrations HbO$_2$ of the healthy zone ZS and the zone to be characterized ZC, and respectively, a difference between the deoxyhaemoglobin concentrations Hb of the healthy zone ZS and the zone to be characterized ZC, and $\Delta Dif$ represents an average value, such as the arithmetic mean, of the difference or differences between the determined values of the diffusion coefficient $\mu_s$ of the healthy zone ZS and the zone to be characterized ZC, the average being for example, calculated for wave length ranges indicated here above, that is [450 nm; 800 nm], preferably [650 nm; 800 nm], and even more preferably [740 nm; 760 nm]

In a similar manner, the values of the coefficients $\alpha'_1$, $\beta'_1$, $\gamma'_1$ and $\delta'_1$ are, for example, predetermined in an empirical manner based on tests performed on a set of patients.

By way of example, for a tuberculin skin test, the values of the coefficients $\alpha'_1$, $\beta'_1$, $\gamma'_1$ and $\delta'_1$ are respectively equal to 1.741, −0.007, −0.147 and −0.434, as will subsequently be described herein for the equation (23).

Figure 7:
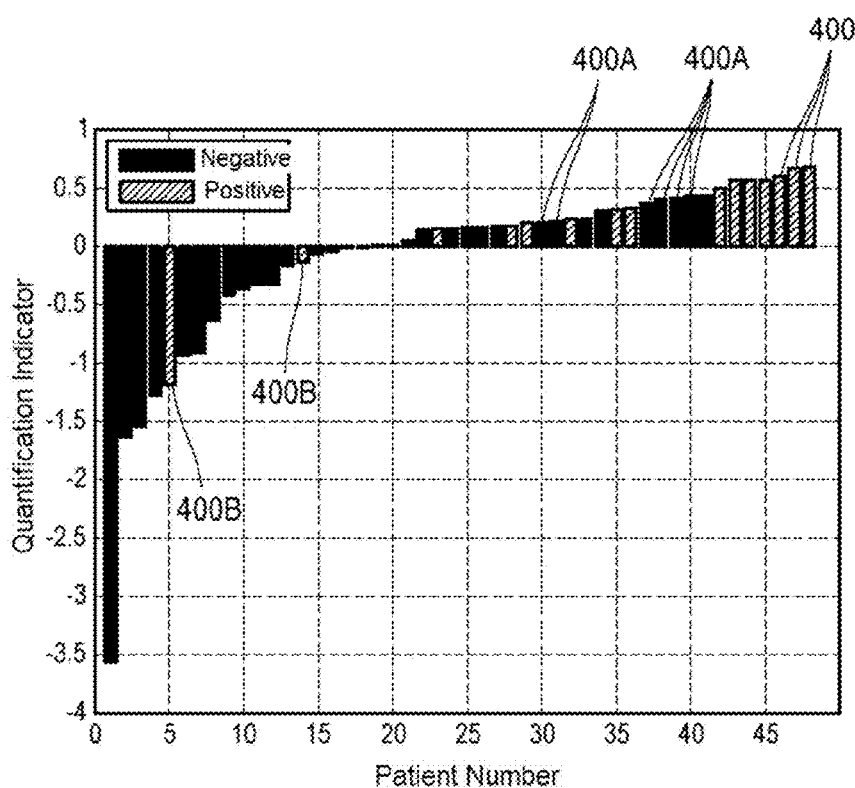
FIG. 7 is a histogram representing values for the quantification indicator calculated for a plurality of patients by implementing a method of the state of the art.

The results obtained with the method of the prior art for a group of 48 patients during clinical trials are illustrated in the histogram shown in FIG. 7, representing in the form of bars 400, the values of the quantification indicator IND calculated for each of the 48 tests on patients, the tests being identified by the respective numbers on the abscissa (X axis) ranging from 1 to 48. In the example in FIG. 7, the quantification indicator IND satisfies the following equation:

$$IND = -0.070 - 0.128 \times Ox - 0.026 \times Deox \quad (22)$$

It may be observed that there exist many diagnostic errors for the test of the dermal reaction, that is to say, cases where the reaction is indicated incorrectly as positive (false positive), with the bars then being referenced as 400A, and on the contrary, there are cases where the reaction is indicated as negative whereas it is in actual fact positive (false negative), with the bars thus being referenced as 400B. In the example shown in FIG. 7, 17 false positive cases and 3 false negative cases have been enumerated, which is 20 errors out of 48 tests, that is to say, an error rate equal to 42%.

By comparison, the results obtained with the method according to the invention for the same group of 48 tests on patients are illustrated in the histogram shown in FIG. 8, representing in the form of bars 500, the values of the quantification indicator IND calculated for each of said tests, also identified by the respective numbers on the abscissa (X axis) ranging from 1 to 48. The results in FIG. 8 correspond to the case where the quantification indicator IND is calculated in accordance with the equation (21). In the example shown in FIG. 8, the quantification indicator IND satisfies the following equation:

$$IND = 1.741 - 0.007 \times \Delta Ox - 0.147 \times \Delta Deox - 0.434 \times \Delta Dif \quad (23)$$

It may thus be observed that the number of diagnostic errors is indeed much lower with the method according to the invention than with the method according to the state of the art. In fact, in the example shown in FIG. 8, only five errors have been enumerated for 48 tests, which indicates an error rate equal to 10%, that is to say, approximately four times lower than the error rate of the state of the art. The errors in this example are 4 false positive cases, with the bars thus being referenced as 500A, and one false negative case, said bar being referenced as 500B.

In the example shown in FIGS. 7 and 8, the quantification indicators IND are calculated 72 hours after the original stimulation causing the dermal reaction.

It was then found that it is possible to calculate within a time period of less than 72 hours the quantification indicator IND by following the method of calculation according to the invention, while also maintaining a low error rate. Thus, it has been possible to establish sufficiently reliable indicators, which allow for earlier quantification of the reaction, it being possible to reduce the time period between the injection and the reading to 18 hours.

With the method according to the invention, taking into account the coefficient of diffusion $\mu_s$ in calculating the quantification indicator IND provides the ability particularly to better detect an induration.

It has further been found that the results obtained are best when the quantification indicator IND is calculated in accordance with the equation (21) rather than in accordance with the equation (20).

It may thus be understood that the method and the system of computation 10 according to the invention provide for improving the relevance of the calculated quantification indicator IND, while at the same time making it possible to calculate this indicator IND within the shortest possible time frame after the original stimulation causing the dermal reaction.

FIG. 9 corresponds to a further example in which elements that are identical to the example previously described above are identified by identical reference numerals, and are not being described again.

According to this example, the second calculation software 40 is adapted for calculating the quantification indicator IND on the basis of the previously calculated concentration of the or each chromophore, the or each determined value of the diffusion coefficient $\mu_s$, and also on the basis of the or each determined value of the absorption coefficient $\mu_a$.

Alternatively, the second calculation software 40 is adapted for calculating the quantification indicator IND on the basis of a difference between the concentrations of the or each chromophore Hb, HbO$_2$ of the healthy zone ZS and the zone to be characterized ZC, on the basis of the difference or differences between the determined values of the diffusion coefficient $\mu_s$ of the healthy zone ZS and the zone to be characterized ZC, and on the basis of the difference or differences between the determined values of the absorption coefficient $\mu_a$ of the healthy zone ZS and the zone to be characterized ZC.

According to this further example, the indicator IND, calculated during the step 140 by making use of the second calculation software 40, is a function of: the concentration of the or each chromophore HbO$_2$, Hb previously calculated, the or each determined value of the diffusion coefficient $\mu_s$ of the zone to be characterized ZC, and also of the or each determined value of the absorption coefficient $\mu_a$ of the zone to be characterized ZC.

The quantification indicator IND is preferably calculated based on an average value, such as the arithmetic mean, of a plurality of values of the diffusion coefficient $\mu_s$ of the zone to be characterized ZC, these values of the diffusion coefficient $\mu_s$ being determined for a plurality of values of the wave length $\lambda$, for example comprised between 450 nm and 800 nm, preferably between 650 nm and 800 nm, and even more preferably between 740 nm and 760 nm.

The quantification indicator IND is also preferably calculated based on an average value, such as the arithmetic mean, of a plurality of values of the absorption coefficient $\mu_a$ of the zone to be characterized ZC, these values of the absorption coefficient $\mu_a$ being determined for a plurality of values of the wave length $\lambda$, of the light beam, for example comprised between 450 nm and 800 nm, preferably between 450 nm and 700 nm, and even more preferably between 500 nm and 650 nm.

The quantification indicator IND then satisfies, for example, the following equation:

$$IND = \alpha_2 + \beta_2 \times Ox + \gamma_2 \times Deox + \delta_2 \times Dif + \epsilon_2 \times Abs \quad (24)$$

where IND represents the quantification indicator for quantifying the dermal reaction, $\alpha_2$, $\beta_2$, $\gamma_2$, $\delta_2$ and $\epsilon_2$ are predetermined coefficients for a given value of the time period between the moment of measurement of the spectrum M of the back scattered radiation and the moment of injection of the active ingredient, with $\beta_2$, $\gamma_2$, $\delta_2$ and $\epsilon_2$ having non-null values, Dif represents the average, such as the arithmetic mean, of the determined value or values of the diffusion coefficient $\mu_s$ calculated for the wave length ranges indicated here above, that is [450 nm; 800 nm], preferably [650 nm; 800 nm], and even more preferably [740 nm; 760 nm], and Abs represents the average, such as the arithmetic mean, of the determined value or values of the absorption coefficient $\mu_a$ calculated for the wave length ranges indicated here above, that is [450 nm; 800 nm], preferably [450 nm; 700 nm], and even more preferably [500 nm; 650 nm].

The values of the coefficients $\alpha_2$, $\beta_2$, $\gamma_2$ $\delta_2$ and $\epsilon_2$ are, for example, predetermined in an empirical manner based on tests performed on a set of patients. This predetermination is done preferably via a discriminant factor analysis. By way of a variant, the predetermination is done via a principal component analysis.

Alternatively, the quantification indicator IND is computed based on a difference between the concentrations of the or each chromophore Hb, HbO$_2$ of the healthy zone ZS and the zone to be characterized ZC, on the basis of the difference or differences between the determined values of the diffusion coefficient $\mu_s$ of the healthy zone ZS and the zone to be characterized ZC, and on the basis of the difference or differences between the determined values of the absorption coefficient $\mu_a$ of the healthy zone ZS and the zone to be characterized ZC.

According to this variant, the quantification indicator IND then satisfies, for example, the following equation:

$$IND = \alpha'_2 + \beta'_2 \times \Delta Ox + \gamma'_2 \times \Delta Deox + \delta'_2 \times \Delta Dif + \epsilon'_2 \times \Delta Abs \quad (25)$$

where IND represents the quantification indicator for quantifying the dermal reaction, $\alpha'_2$, $\beta'_2$, $\gamma'_2$, $\delta'_2$ and $\epsilon'_2$ are predetermined coefficients for a given value of the time period between the moment of measurement of the spectrum of the back scattered radiation and the moment of injection of the active ingredient, with $\beta'_2$, $\gamma'_2$, and $\delta'_2$ having non-null values, $\Delta Ox$ and $\Delta Deox$ represent a difference between the oxyhaemoglobin concentrations HbO$_2$ of the healthy zone ZS and the zone to be characterized ZC, and respectively, a difference between the deoxyhaemoglobin concentrations Hb of the healthy zone ZS and the zone to be characterized ZC, and $\Delta Dif$ and $\Delta Abs$ represent an average value, such as the arithmetic mean, of the difference or differences between the determined values of the diffusion coefficient $\mu_s$ of the healthy zone ZS and the zone to be characterized ZC, and respectively, of the difference or differences between the determined values of the absorption coefficient $\mu_a$ of the healthy zone ZS and the zone to be characterized ZC.

The average value for obtaining $\Delta Dif$ is, for example, calculated for the wave length ranges indicated here above, that is [450 nm; 800 nm], preferably [650 nm; 800 nm], and even more preferably [740 nm; 760 nm], and that for obtaining $\Delta Abs$ is, for example, calculated for the wave length ranges indicated here above, that is [450 nm; 800 nm], preferably [450 nm; 700 nm], and even more preferably [500 nm; 650 nm].

In a similar manner, the values of the coefficients $\alpha'_2$, $\beta'_2$, $\gamma'_2$, $\delta'_2$ and $\epsilon'_2$ are, for example, predetermined in an empirical manner based on tests performed on a set of patients.

By way of example, the values of the coefficients $\alpha_2$, $\beta_2$, $\gamma_2$, $\delta_2$ and $\epsilon_2$ are respectively equal to 1.841, −0.128, −0.181, −0.463 and 0.324, as will be subsequently described herein for the equation (26) here below.

The results obtained with the method according to the further example of the invention for the same group of 48 tests, as has been indicated for previous FIGS. 7 and 8, are illustrated in the histogram shown in FIG. 9, representing in the form of bars 550 the values of the quantification indicators IND 48 calculated for each of said patients, also identified by the respective numbers on the abscissa (X axis) ranging from 1 to 48. The results in FIG. 9 correspond to the case where the quantification indicator IND is calculated in accordance with the equation (25). In the example shown in FIG. 9, the quantification indicator IND satisfies the following equation:

$$IND = 1.841 - 0.128 - Ox - 0.181 \times Deox - 0.463 \times Dif + 0.324 \times Abs \quad (26)$$

It may thus be observed that the number of diagnostic errors is indeed lower still with the method according to the further example than with the method according to the above example, and more significantly so, than with the method of the state of the art. In fact, in the example shown in FIG. 9, only four errors have been enumerated for 48 patients, which indicates an error rate equal to 8%, that is to say, approximately 5.5 times lower than the error rate of the state of the art. The errors in this example are 3 false positive cases, with the bars thus being referenced as 550A, and one false negative case, said bar being referenced as 550B.

In the example shown in FIGS. 7 and 9, the quantification indicators IND are calculated 72 hours after the original stimulation causing the dermal reaction.

It was then also found that it is possible to calculate within a time period substantially less than 72 hours the quantification indicator IND by following the method of calculation according to the further example, while also maintaining a low error rate. Thus, it has been possible to establish sufficiently reliable indicators, which allow for earlier quantification of the reaction, it being possible to reduce the time period between the injection and the reading to 18 hours.

It has further been found that the results obtained are best when the quantification indicator IND is calculated in accordance with the equation (25), rather than in accordance with the equation (24).

It may thus be understood that the method and the system of computation 10 according to the further example of the invention provide for improving the relevance of the calculated quantification indicator IND, while at the same time making it possible to calculate this indicator IND within the shortest possible time frame after the original stimulation causing the dermal reaction.

The invention claimed is:

1. A method calculating a quantification indicator for quantifying a dermal reaction on the skin of a living being, the skin having a plurality of chromophores, the method comprising the following steps:

illuminating a zone to be characterized on the skin via an excitation light beam emitted by a source of light, the skin reaction being included in the zone to be characterized, measuring, using a spectrometer, a spectrum of a back scattered radiation coming from the skin as a result of the illumination of said zone to be characterized, determining, on the basis of the measured spectrum and for at least one given value of the wavelength of the light beam, a value of the absorption coefficient for the zone to be characterized, calculating, on the basis of the or each determined value of the absorption coefficient, a concentration of at least one chromophore in the skin, determining, on the basis of the measured spectrum and for at least one given value of the wavelength of the light beam, a value of a diffusion coefficient for the zone to be characterized, calculating the quantification indicator quantifying the dermal reaction on the basis of the previously calculated concentration of the or each chromophore, calculating the quantification indicator quantifying the dermal reaction also on the basis of the or each determined value of the diffusion coefficient, wherein the quantification indicator quantifying the dermal reaction (IND) satisfies the following equation:

$$IND = \alpha + \beta \cdot Ox + \gamma \cdot Deox + \delta \cdot Dif + \epsilon \cdot Abs$$

where IND represents the quantification indicator quantifying the dermal reaction, $\alpha$, $\beta$, $\gamma$, $\delta$, and $\epsilon$ are predetermined coefficients for a given value of a time period between a moment of measurement of the spectrum of a back scattered radiation and a moment of injection of the active ingredient, with $\beta$, $\gamma$ and $\delta$ having non-zero values, Ox and Deox represent an oxyhaemoglobin concentration and deoxyhaemoglobin concentration, respectively, for zone to be characterized, and Dif and Abs represent an average value, respectively, of the determined value or values of the diffusion coefficient of the zone to be characterized and of the detemined values or values of the absorption coefficient of the zone to be characterized.

2. The method of claim 1, wherein, during the step of calculating, the quantification indicator quantifying the dermal reaction is calculated furthermore on the basis of the or each determined value of the absorption coefficient.

3. The method of claim 2, wherein the quantification indicator quantifying the dermal reaction is calculated on the basis of an average value of a plurality of values of the absorption coefficient, determined for a plurality of values of the wavelength of the light beam comprised between at least one of a range of 450 nm and 800 nm, 450 nm and 700 nm, and 500 nm and 650 nm.

4. The method of claim 1, wherein the quantification indicator quantifying the dermal reaction is calculated on the basis of an average value, of a plurality of values of the diffusion coefficient, determined for a plurality of values of the wavelength of the light beam comprised between at least one of a range of 450 nm and 800 nm, 650 nm and 800 nm, and 740 nm and 760 nm.

5. A method calculating a quantification indicator for quantifying a dermal reaction on the skin of a living being, the skin having a plurality of chromophores, the method comprising the following steps:

illuminating a zone to be characterized on the skin via an excitation light beam emitted by a source of light, the skin reaction being included in the zone to be characterized, measuring, using a spectrometer, a spectrum of a back scattered radiation coming from the skin as a result of the illumination of said zone to be characterized, determining, on the basis of the measured spectrum and for at least one given value of the wavelength of the light beam, a value of the absorption coefficient for the zone to be characterized, calculating, on the basis of the or each determined value of the absorption coefficient, a concentration of at least one chromophore in the skin, wherein during the step of calculating the concentration of the chromophore or chromophores, the concentration of the chromophore or chromophores, the concentration of the chromophore or chromophores is also calculated for a healthy zone of the skin on the basis of the value or values of the absorption coefficient for said healthy zone, determining, on the basis of the measured spectrum and for at least one given value of the wavelength of the light beam, a value of a diffusion coefficient for the zone to be characterized, calculating the quantification indicator quantifying the dermal reaction on the basis of the previously calculated concentration of the or each chromophore, calculating the quantification indicator quantifying the dermal reaction also on the basis of the or each determined value of the diffusion coefficient, wherein the quantification indicator quantifying the dermal reaction (IND) satisfies the following equation:

$$IND = \alpha' + \beta' \cdot \Delta Ox + \gamma' \cdot \Delta Deox + \delta' \cdot \Delta Dif + \epsilon' \cdot \Delta Abs$$

where IND represents the quantification indicator quantifying the dermal reaction, $\alpha'$, $\beta'$, $\gamma'$, $\delta'$, and $\epsilon'$ are predetermined coefficients for a given value of a time period between a moment of measurement of the spectrum of a back scattered radiation and a moment of injection of the active ingredient, with $\beta'$, $\gamma'$ and $\delta'$ having non-zero values, $\Delta Ox$ and $\Delta Deox$ represent, respectively, a difference between an oxyhaemoglobin concentrations of the healthy zone and the zone to be characterized, and a difference between a deoxyhaemoglobin concentration of the healthy zone and the zone to be characterized, and $\Delta Dif$ and $\Delta Abs$ represent an average value, respectively, of a difference or differences between the determined values of the diffusion coefficient of the healthy zone and the zone to be characterized and of a difference or differences between the determined values of the absorption coefficient of the healthy zone and the zone to be characterized, and wherein the quantification indicator quantifying the dermal reaction is calculated on the basis of a difference between the concentrations of the or each chromophore of the healthy zone and of the zone to be characterized and on the basis of the difference or differences between the determined values of the diffusion coefficient of the healthy zone and the zone to be characterized.

6. The method of claim 5, wherein, during the step of calculating, the quantification indicator quantifying the dermal reaction is calculated additionally on the basis of the difference or differences between the determined values of the absorption coefficient of the healthy zone, and the zone to be characterized.

7. The method of claim 1, wherein the zone of the skin is illuminated via an excitation optical fibre, and measurement of the spectrum is performed via a plurality of detection optical fibres connected to the spectrometer, the detection fibres being at different distances from the excitation fibre, and wherein the determination, for at least one given value of the wavelength of the light beam, the value of the determination, for at least one given value of the wavelength of the light beam, of the value of the absorption coefficient, and the diffusion coefficient, respectively, is performed on the basis of the measured spectra for said different distances.

8. The method of claim 1, wherein the method further comprises predetermining a reference table including a plurality of values of the reflectance of the skin, each value of said table being predetermined for a respective pair of values of the absorption coefficient and the diffusion coefficient, in which at least one value of the reflectance of the zone to be characterized is measured with the use of the spectrometer during the step of measurement, and during the step of determination of the absorption coefficient and the diffusion coefficient, the pair of determined values of the absorption coefficient and the diffusion coefficient is that which minimises the error between the predetermined reflectance values of the reference table and the measured reflectance value or values.

9. The method of claim 8, wherein the zone of the skin is illuminated via an excitation optical fibre, and measurement of the spectrum is performed via a plurality of detection optical fibres connected to the spectrometer, the detection fibres being at different distances from the excitation fibre, and wherein predetermining the reference table is carried out for said different distances, each value of said table being predetermined for a respective pair of values of the absorption coefficient and the diffusion coefficient and for said different distances, at least one value of the reflectance of the zone to be characterized being measured for each of said distances and with the use of the spectrometer during the measurement step.

10. The method of claim 1, wherein, during the step of calculating the concentration of the chromophore or chromophores, the concentration of the chromophore or chromophores is firstly calculated for a healthy zone of the skin on the basis of the value or values of the absorption coefficient for said healthy zone, and the concentration of the chromophore or chromophores is then calculated for the zone to be characterized on the basis of the concentration of the chromophore or chromophores for said healthy zone and of the value or values of the absorption coefficient for said zone to be characterized.

11. The method of claim 1, wherein the or each chromophore is selected from the group consisting of: water, melanin, oxyhaemoglobin, deoxyhaemoglobin and bilirubin.

12. A computing system calculating a quantification indicator quantifying a dermal reaction on the skin of a living being, the skin having a plurality of chromophores, the system comprising the following:

a light source emitting an excitation light beam in order to illuminate a zone to be characterized on the skin, the skin reaction being included in the zone to be characterized, a spectrometer measuring a spectrum of a back scattered radiation coming from the skin as a result of the illumination of said zone to be characterized, an information processing unit comprising:

a first absorbent coefficient calculator determining, on the basis of the measured spectrum from the spectrometer and for at least one given value of the wavelength of the light beam, a value of the absorption coefficient for the zone to be characterized, a first calculator calculating, on the basis of the or each determined value of the absorption coefficient, a concentration of at least one chromophore in the skin, a second calculator calculating the quantification indicator quantifying a dermal reaction on the basis of the previously calculated concentration of the or each chromophore, the first absorbent coefficient calculator determining, on the basis of the measured spectrum from the spectrometer, and for at least one given value of the wavelength of the light beam, a value of a diffusion coefficient for the zone to be characterized, the second calculator calculates the quantification indicator for quantifying the dermal reaction also on the basis of the or each determined value of the diffusion coefficient, wherein the quantification indicator quantifying the dermal reaction (IND) satisfies the following equation:

$$IND = \alpha + \beta \cdot Ox + \gamma \cdot Deox + \delta \cdot Dif + \epsilon \cdot Abs$$

where IND represents the quantification indicator quantifying the dermal reaction, $\alpha$, $\beta$, $\gamma$, $\delta$, and $\epsilon$ are predetermined coefficients for a given value of a time period between a moment of measurement of the spectrum of a back scattered radiation and a moment of injection of the active ingredient, with β, γ and δ having non-zero values, Ox and Deox represent an oxyhaemoglobin concentration and deoxyhaemoglobin concentration, respectively, for the zone to be characterized, Dif and Abs represent an average value, respectively, of the determined value or values of the diffusion coefficient of the zone to be characterized and of the determined value or values of the absorption coefficient of the zone to be characterized.

13. A computing system calculating a quantification indicator quantifying a dermal reaction on
the skin of a living being, the skin having a plurality of chromophores,
the system comprising the following:
a light source emitting an excitation light beam in order to illuminate a zone to be characterized on the skin, the skin reaction being included in the zone to be characterized,
a spectrometer measuring a spectrum of a back scattered radiation coming from the skin as a result of the illumination of said zone to be characterized,
an information processing unit comprising:
    a first absorbent coefficient calculator determining, on the basis of the measured spectrum from the spectrometer and for at least one given value of the wavelength of the light beam, a value of the absorption coefficient for the zone to be characterized,
    a first calculator calculating, on the basis of the or each determined value of the absorption coefficient, a concentration of at least one chromophore in the skin, and calculating the concentration of the chromophore or chromophores, the concentration of the chromophore or chromophores is also calculated for a healthy zone of the skin on the basis of the value or values of the absorption coefficient for said healthy zone,
    a second calculator calculating the quantification indicator quantifying the dermal reaction on the basis of the previously calculated concentration of the or each chromophore,
    the first absorbent coefficient calculator further determines, on the basis of the measured spectrum from the spectrometer, and for at least one given value of the wavelength of the light beam, a value of a diffusion coefficient for the zone to be characterized
    the second calculator calculates the quantification indicator for quantifying the dermal reaction also on the basis of the or each determined value of the diffusion coefficient,
wherein the quantification indicator quantifying the dermal reaction (IND) satisfies the following equation:

$$IND = \alpha' + \beta' \cdot \Delta Ox + \gamma' \cdot \Delta Deox + \delta' \cdot \Delta Dif + \epsilon' \cdot \Delta Abs$$

where IND represents the quantification indicator quantifying the dermal reaction, $\alpha'$, $\beta'$, $\gamma'$, $\delta'$, and $\epsilon'$ are predetermined coefficients for a given value of a time period between a moment of measurement of the spectrum of a back scattered radiation and a moment of injection of the active ingredient, with $\beta'$, $\gamma'$ and $\delta'$ having non-zero values, $\Delta Ox$ and $\Delta Deox$ represent, respectively, a difference between an oxyhaemoglobin concentrations of the healthy zone and the zone to be characterized, and a difference between a deoxyhaemoglobin concentration of the healthy zone and the zone to be characterized, and $\Delta Dif$ and $\Delta Abs$ represent an average value, respectively, of a difference or differences between the determined values of the diffusion coefficient of the healthy zone and the zone to be characterized and of a difference or differences between the determined values of the absorption coefficient of the healthy zone and the zone to be characterized.

14. The method of claim 5, wherein, during the step of calculating, the quantification indicator quantifying the dermal reaction is calculated furthermore on the basis of the or each determined value of the absorption coefficient.

15. The method of claim 14, wherein the quantification indicator quantifying the dermal reaction is calculated on the basis of an average value of a plurality of values of the absorption coefficient, determined for a plurality of values of the wavelength of the light beam comprised between at least one of a range of 450 nm and 800 nm, 450 nm and 700 nm, and 500 nm and 650 nm.

16. The method of claim 5, wherein the quantification indicator quantifying the dermal reaction is calculated on the basis of an average value, of a plurality of values of the diffusion coefficient, determined for a plurality of values of the wavelength of the light beam comprised between at least one of a range of 450 nm and 800 nm, 650 nm and 800 nm, and 740 nm and 760 nm.

17. The method of claim 5, wherein the zone of the skin is illuminated via an excitation optical fibre, and measurement of the spectrum is performed via a plurality of detection optical fibres connected to the spectrometer, the detection fibres being at different distances from the excitation fibre, and
wherein the determination, for at least one given value of the wavelength of the light beam, the value of the determination, for at least one given value of the wavelength of the light beam, of the value of the absorption coefficient, and the diffusion coefficient, respectively, is performed on the basis of the measured spectra for said different distances.

18. The method of claim 5, wherein the method further comprises predetermining a reference table including a plurality of values of the reflectance of the skin, each value of said table being predetermined for a respective pair of values of the absorption coefficient and the diffusion coefficient, in which at least one value of the reflectance of the zone to be characterized is measured with the use of the spectrometer during the step of measurement, and during the step of determination of the absorption coefficient and the diffusion coefficient, the pair of determined values of the absorption coefficient and the diffusion coefficient is that which minimises the error between the predetermined reflectance values of the reference table and the measured reflectance value or values.

19. The method of claim 18, wherein the zone of the skin is illuminated via an excitation optical fibre, and measurement of the spectrum is performed via a plurality of detection optical fibres connected to the spectrometer, the detection fibres being at different distances from the excitation fibre, and
wherein predetermining the reference table is carried out for said different distances, each value of said table being predetermined for a respective pair of values of the absorption coefficient and the diffusion coefficient and for said different distances, at least one value of the reflectance of the zone to be characterized being measured for each of said distances and with the use of the spectrometer during the measurement step.

20. The method of claim 5, wherein, during the step of calculating the concentration of the chromophore or chromophores, the concentration of the chromophore or chromophores is firstly calculated for a healthy zone of the skin on the basis of the value or values of the absorption coefficient for said healthy zone, and the concentration of the chromophore or chromophores is then calculated for the zone to be characterized on the basis of the concentration of the chromophore or chromophores for said healthy zone and of the value or values of the absorption coefficient for said zone to be characterized.

21. The method of claim 5, wherein the or each chromophore is selected from the group consisting of: water, melanin, oxyhaemoglobin, deoxyhaemoglobin and bilirubin.

22. The method of claim 5, wherein the or each chromophore is calculated from the oxyhaemoglobin concentration and the deoxyhaemoglobin concentration.

23. The method of claim 1, wherein the or each chromophore is calculated from the oxyhaemoglobin concentration and the deoxyhaemoglobin concentration.

* * * * *